(12) United States Patent
Nakano

(10) Patent No.: US 11,951,290 B2
(45) Date of Patent: Apr. 9, 2024

(54) MEDICAL SYRINGE, GASKET FOR USE IN THE SYRINGE, AND PRODUCTION METHOD FOR THE GASKET

(71) Applicant: Sumitomo Rubber Industries, Ltd., Hyogo (JP)

(72) Inventor: Hiroaki Nakano, Kobe (JP)

(73) Assignee: Sumitomo Rubber Industries, Ltd., Hyogo (JP)

( * ) Notice: Subject to any disclaimer, the term of this patent is extended or adjusted under 35 U.S.C. 154(b) by 527 days.

(21) Appl. No.: 17/116,211

(22) Filed: Dec. 9, 2020

(65) Prior Publication Data

US 2021/0196897 A1 Jul. 1, 2021

(30) Foreign Application Priority Data

Dec. 26, 2019 (JP) ................................. 2019-236121

(51) Int. Cl.
| | |
|---|---|
| *B29C 35/02* | (2006.01) |
| *A61M 5/31* | (2006.01) |
| *A61M 5/315* | (2006.01) |
| *B29C 59/00* | (2006.01) |
| *B29K 23/00* | (2006.01) |

(52) U.S. Cl.
CPC ...... *A61M 5/31515* (2013.01); *A61M 5/3134* (2013.01); *A61M 5/31513* (2013.01); *A61M 5/31576* (2013.01); *B29C 35/02* (2013.01); *B29C 59/007* (2013.01); *A61M 2207/00* (2013.01); *B29C 2791/009* (2013.01); *B29K 2023/22* (2013.01)

(58) Field of Classification Search
None
See application file for complete search history.

(56) References Cited

U.S. PATENT DOCUMENTS

| | | | |
|---|---|---|---|
| 10,363,371 | B2 | 7/2019 | Nakano et al. |
| 2003/0114802 | A1 | 6/2003 | Chung et al. |
| 2006/0178643 | A1 | 8/2006 | Sudo et al. |
| 2013/0040156 | A1 | 2/2013 | Nakano et al. |
| 2013/0316110 | A1 | 11/2013 | Sudo |
| 2016/0287800 | A1 | 10/2016 | Nakano et al. |
| 2017/0021107 | A1 | 1/2017 | Kaneko et al. |
| 2017/0281873 | A1* | 10/2017 | Kaneko ................... B29C 69/00 |

(Continued)

FOREIGN PATENT DOCUMENTS

| | | | | |
|---|---|---|---|---|
| EP | 3409311 | A1 * | 12/2018 | ............ A61M 5/178 |
| JP | H07-25953 | Y2 | 6/1995 | |

(Continued)

OTHER PUBLICATIONS

Yotsutsuji WO2017175256A1 2017 English Translation (Year: 2017).*

*Primary Examiner* — Jacob T Minskey
*Assistant Examiner* — Adrien J Bernard
(74) *Attorney, Agent, or Firm* — Studebaker & Brackett PC

(57) ABSTRACT

A gasket includes a main body made of an elastic material, and a film laminated on the surface of the main body. The gasket has a film circumferential surface portion to be brought into contact with an inner peripheral surface of a syringe barrel, and an annular groove formed circumferentially of the film circumferential surface portion. The gasket further includes an annular member which is fixed in the annular groove and includes an annular projection projecting from the surface of the film.

10 Claims, 3 Drawing Sheets

(56) References Cited

U.S. PATENT DOCUMENTS

| | | | |
|---|---|---|---|
| 2018/0036489 A1 | 2/2018 | Nakano et al. | |
| 2018/0177951 A1 * | 6/2018 | Sakashita | A61M 5/24 |
| 2018/0369489 A1 | 12/2018 | Nakano et al. | |
| 2020/0338272 A1 | 10/2020 | Yotsutsuji | |

FOREIGN PATENT DOCUMENTS

| | | | |
|---|---|---|---|
| JP | 3282322 B2 | 5/2002 | |
| JP | 2003-190283 A | 7/2003 | |
| JP | 2004-162761 A | 6/2004 | |
| JP | 2006-181027 A | 7/2006 | |
| JP | 4908617 B2 | 4/2012 | |
| JP | 2015-146871 A | 8/2015 | |
| JP | 2016-209081 A | 12/2016 | |
| JP | 2017-023459 A | 2/2017 | |
| JP | WO2017175256 A1 * | 10/2017 | A61M 5/315 |
| JP | 2018-019910 A | 2/2018 | |
| WO | 2017/168461 A1 | 10/2017 | |

* cited by examiner

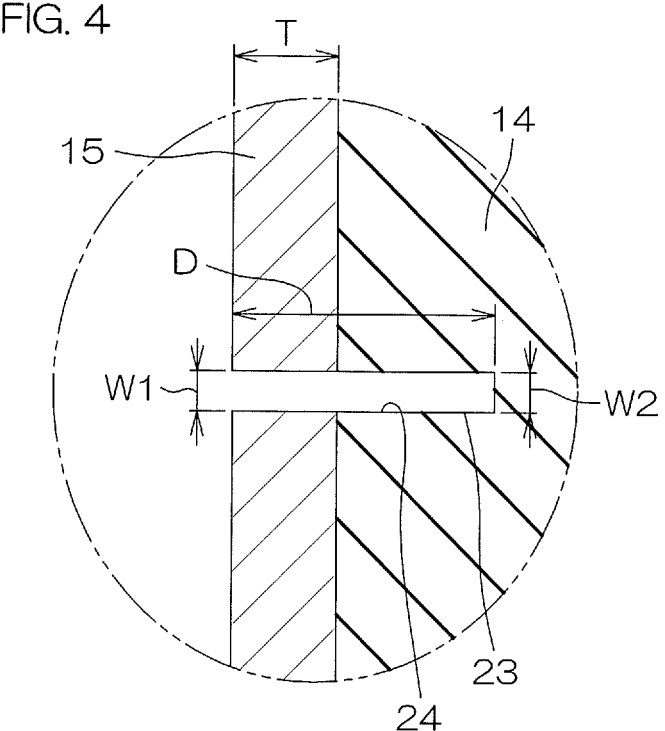

MEDICAL SYRINGE, GASKET FOR USE IN THE SYRINGE, AND PRODUCTION METHOD FOR THE GASKET

TECHNICAL FIELD

The present invention relates to a medical syringe, a gasket for use in the syringe, and a production method for the gasket.

BACKGROUND ART

For medical syringes, a laminate gasket including a rubber gasket body and a film covering the surface of the gasket body is widely used. According to this laminate gasket, the film covering the surface of the rubber gasket body prevents a vulcanized rubber component from migrating into a liquid drug contained in such a medical syringe, and ensures proper slidability of the laminate gasket as compared with the rubber.

CITATION LIST

Patent Document

Patent Document 1: JP-HEI7(1995)-25953U

SUMMARY OF THE INVENTION

Problem to be Solved by the Invention

More specifically, it is known that various vulcanization components are present in the vulcanized rubber, and these vulcanization components and thermal decomposition products of the vulcanization components are liable to migrate into the liquid drug when being kept in contact with the liquid drug. It is also known that the efficacy and the stability of a certain liquid drug is influenced by the components migrating into the liquid drug.

Further, the gasket is required to be smoothly slid when the syringe is used. In general, a gasket made of the vulcanized rubber is less slidable. To cope with this, silicone oil is generally applied to the inner surface of the syringe barrel of the syringe. However, it is also known that the efficacy and the stability of a certain liquid drug is influenced by the silicone oil.

In view of the foregoing, the laminate gasket including the rubber gasket body and the highly slidable film laminated on the surface of the rubber gasket body is often used for the medical syringe.

However, the film laminated on the surface of the gasket body of the laminate gasket has no elasticity, thereby impairing the elasticity of the inside vulcanized rubber.

The elasticity of the gasket is an essential requirement for reliable sealing of the liquid drug contained in the syringe barrel. If the gasket has an insufficient elasticity, the liquid drug is disadvantageously liable to leak out of the syringe barrel.

In particular, a syringe (so-called "prefilled syringe") preliminarily filled with a liquid drug is required to serve as a container capable of reliably confining the liquid drug for a longer period of time. Therefore, it is imperative to suppress the leakage of the liquid drug.

To cope with this, the inventors of the present invention conducted additional studies and, as a result, contemplated that a minute annular projection is additionally formed on the film laminated on a circumferential surface portion of the gasket.

However, the minute annular projection formed on the film is liable to be separated from the film under severe use conditions in which the gasket is repeatedly slid in the syringe barrel. The separation of the annular projection makes it impossible to reliably seal the liquid drug, resulting in leakage of the liquid drug.

In view of the foregoing, it is an object of the present invention to provide a medical syringe capable of maintaining a higher sealability and preventing the leakage of the liquid drug even if the gasket is repeatedly slid therein, a gasket for the medical syringe, and a production method for the gasket.

Solution to Problems

According to one aspect of the present invention, a gasket for use in a medical syringe is provided, which includes a main body made of an elastic material, and a film laminated on a surface of the main body. The gasket has a circumferential surface portion to be brought into contact with an inner peripheral surface of a syringe barrel of the syringe, and the circumferential surface portion has at least one annular groove extending circumferentially thereof. The gasket further includes an annular member fixed in the annular groove and including an annular projection which projects from a surface of the film and extends circumferentially of the circumferential surface portion.

The annular projection may have a height of not less than 1 μm and not greater than 50 μm.

The annular projection may have a width of not less than 1 μm and not greater than 70 μm.

The film may have a thickness of not less than 20 m and not greater than 50 μm.

The annular groove may have a depth of not less than m and not greater than 200 μm.

According to another aspect of the present invention, a medical syringe is provided, which includes a tubular syringe barrel, a plunger combined with the syringe barrel and reciprocally movable in the syringe barrel, and a gasket attached to a distal end of the plunger, wherein the gasket is the inventive gasket described above.

The medical syringe may be a prefilled syringe in which the syringe barrel is prefilled with a liquid drug.

According to further another aspect of the present invention, a method for producing a gasket for a medical syringe includes the steps of: preparing a gasket molding mold; molding a gasket in the mold, the gasket having a surface laminated with a film and including a film circumferential surface portion; removing the gasket from the mold, and then forming an annular groove in the film circumferential surface portion of the gasket circumferentially of the film circumferential surface portion; depositing a fluid material in the formed annular groove and further depositing the fluid material on the annular groove circumferentially of the film circumferential surface portion of the gasket so that the fluid material partly projects from the annular groove; and solidifying the fluid material to fix the fluid material in the annular groove and form an annular member including an annular projection projecting from the surface of the film.

The gasket molding step may include the step of stacking an unvulcanized rubber on an inner surface of the film in the mold, and vulcanization-molding the resulting stack.

The gasket molding step may include the step of roughening the inner surface of the film before stacking the rubber on the inner surface of the film.

The annular groove forming step may include the step of processing the circumferential surface portion of the gasket by a laser beam to remove at least a part of the film according to the shape of the annular groove.

The fluid material may include a fluororesin.

The fluid material may include a metal paste.

The fluid material solidifying step may include a heating step.

Effects of the Invention

According to the present invention, the laminate gasket for the medical syringe is provided, which ensures higher sealability even if the gasket is repeatedly slid in the syringe barrel. Particularly, the laminate gasket is suitable for the prefilled syringe.

According to the present invention, the medical syringe, particularly the prefilled syringe, is provided, which does not influence the efficacy and the stability of the liquid drug even if being kept in contact with the liquid drug for a longer period of time, and ensures higher sealability to prevent the leakage of the liquid drug even if the gasket is repeatedly slid in the syringe barrel.

Further, the present invention provides the production method for the laminate gasket excellent in sealability.

BRIEF DESCRIPTION OF THE DRAWINGS

FIG. 4 is an enlarged sectional view illustrating the portion A of FIG. 2 observed in production of the gasket.

EMBODIMENTS OF THE INVENTION

With reference to the attached drawings, one embodiment of the present invention will hereinafter be described specifically.

Figure 1:
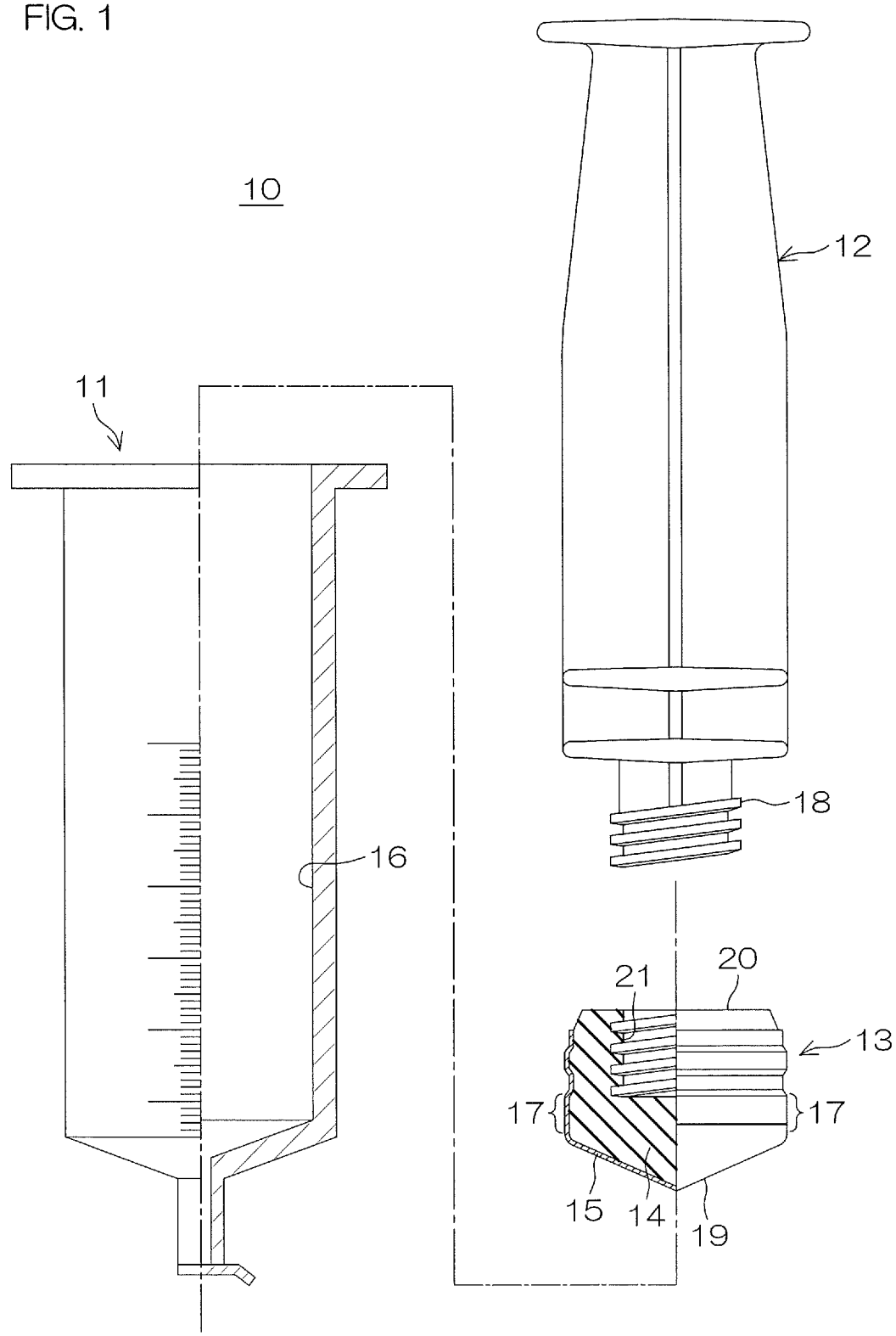
FIG. 1 is an exploded diagram illustrating a medical syringe according to one embodiment of the present invention.

FIG. 1 is an exploded diagram illustrating a medical syringe, i.e., a so-called prefilled syringe, according to the embodiment of the present invention. In FIG. 1, a half of a syringe barrel 11 and a half of a laminate gasket 13 are illustrated in section.

Referring to FIG. 1, the prefilled syringe 10 includes a hollow cylindrical syringe barrel 11, a plunger 12 combined with the syringe barrel 11 and reciprocally movable in the syringe barrel 11, and a laminate gasket 13 attached to a distal end of the plunger 12. The laminate gasket 13 includes a main body 14 made of an elastic material (a rubber or an elastomer) and a film 15 laminated on the surface of the main body 14. The laminate gasket 13 has a circumferential surface portion 17 to be kept in gas-tight and liquid-tight contact with an inner peripheral surface 16 of the syringe barrel 11.

The plunger 12 includes a resin plate piece, for example, having a cross shape as seen in section, and a head 18 provided at a distal end of the resin plate piece and fitted with the laminate gasket 13. The head 18 is an integral part of the plunger 12 made of a resin and shaped in a male screw.

The laminate gasket 13 has a generally cylindrical shape having a short axis. The laminate gasket 13 has a distal end surface 19, for example, having a conical center portion projecting at an obtuse angle, and a rear end face 20 axially recessed into an engagement recess 21 shaped in a female screw. The head 18 of the plunger 12 is screwed into the engagement recess 21 of the laminate gasket 13, whereby the laminate gasket 13 is attached to the distal end of the plunger 12.

Where a liquid drug to be contained in the syringe barrel 11 is free from influence of commonly used silicone oil or curable silicone, the silicone oil or the curable silicone may be applied to the inner peripheral surface 16 of the syringe barrel 11 or on a surface of the laminate gasket 13 to ensure higher slidability of the laminate gasket 13.

Figure 2:
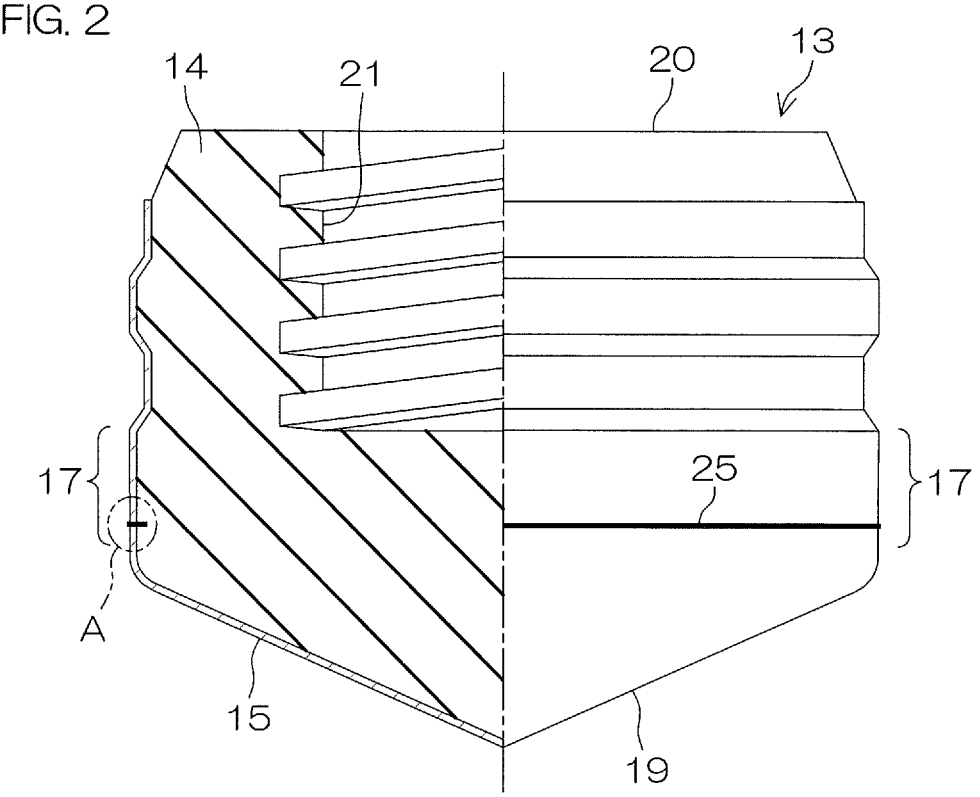
FIG. 2 is a diagram of a laminate gasket according to another embodiment of the present invention with a half thereof illustrated in section.

FIG. 2 is a diagram showing only the laminate gasket 13 of FIG. 1 on an enlarged scale. In FIG. 2, a half of the laminate gasket 13 is illustrated in section.

Referring to FIG. 2, the structure of the laminate gasket 13 according to this embodiment will be described in greater detail.

The laminate gasket 13 includes the main body 14, and the film 15 laminated on the surface of the main body 14. The main body 14 is merely required to be made of the elastic material, which is not particularly limited. Examples of the elastic material include vulcanizable rubbers and thermoplastic elastomers. Of these elastic materials, the vulcanizable rubbers and thermoplastic elastomers of dynamically vulcanizable type having vulcanization sites are more preferred because of their excellent heat resistance. These polymer components for the elastic material are not particularly limited, but preferred examples thereof include ethylene-propylene-diene rubbers and butadiene rubbers which are excellent in moldability. Other preferred examples include butyl rubbers, chlorinated butyl rubbers, and brominated butyl rubbers which are excellent in gas barrier property.

The type of the film 15 to be laminated on the surface of the main body 14 is not particularly limited, as long as the film is capable of preventing migration of components from the vulcanized rubber (main body 14) and has more excellent slidability, i.e., a smaller friction coefficient, than the rubber. Examples of the film include films of ultrahigh molecular weight polyethylenes and fluororesins which are proved to be practical in medical applications.

Particularly, the fluororesin films are preferred because they are excellent in slidability and have chemically stable surfaces. Usable examples of the fluororesins include known fluorine-containing resins such as PTFE, modified PTFE, ethylene tetrafluoroethylene copolymers (ETFE), and perfluoroalkyl ether (PFA). The PTFE and the modified PTFE are preferred because of their excellent slidability and chemical stability. The ETFE is also preferred because of its higher resistance to Y-ray to be used for sterilization. From the viewpoint of adhesion to the main body 14, a film made of a mixture of any of these resins or a laminate film of any of these resins may be used.

An inner surface of the film 15 to be laminated on the main body 14 (to be kept in contact with the main body 14) is preferably processed for adhesion. The method for the adhesion processing is not particularly limited. A preferred example of the adhesion processing is an ion beam processing process which is unlikely to chemically alter the film and obviates the use of an adhesive agent.

Figure 3:
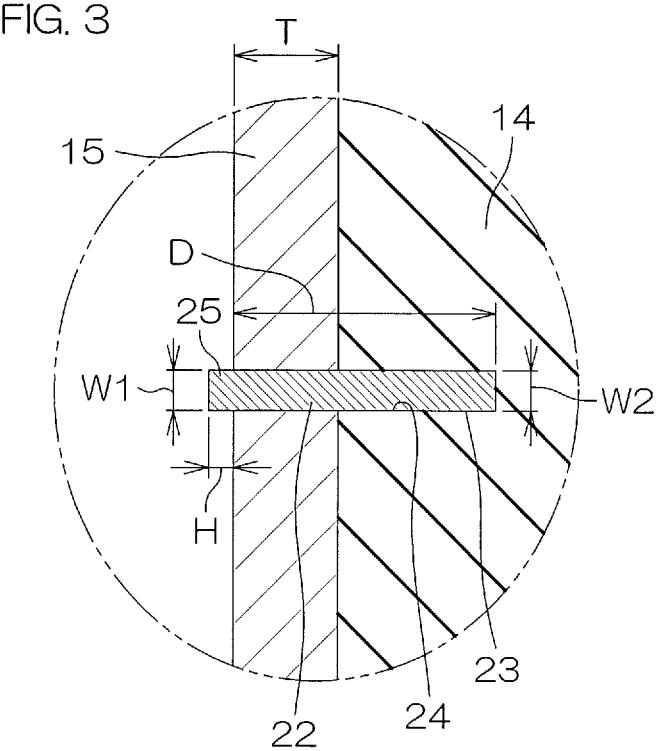
FIG. 3 is an enlarged sectional view illustrating a portion A shown in FIG. 2.

FIG. 3 is an enlarged sectional view illustrating a portion A shown in FIG. 2.

FIG. 4 is an enlarged sectional view illustrating the portion A of FIG. 2 observed in production of the laminate gasket.

The laminate gasket 13 has the circumferential surface portion 17 to be kept in gas-tight and liquid-tight contact with the inner peripheral surface 16 of the syringe barrel 11. The circumferential surface portion 17 is covered with the film 15. The circumferential surface portion 17 is formed with an annular groove 23 (see FIG. 4).

An annular member 22 is fitted in the annular groove 23, and fixed to an inner surface 24 of the annular groove 23.

An outer peripheral portion of the annular member 22 projects from the surface of the film 15 along the entire circumference of the circumferential surface portion 17 to define an annular projection 25 which extends circumferentially of the circumferential surface portion 17.

The annular groove 23 and the annular projection 25 defined by the outer peripheral portion of the annular member 22 fitted in the annular groove 23 extend circumferentially of the circumferential surface portion 17 in an annular form, as implied by their names, with their start points and end points coinciding with each other. With this arrangement, the annular projection 25 provides a uniform liquid drug sealing effect along the entire circumference of the circumferential surface portion 17. Where the circumferential surface portion 17 of the laminate gasket 13 is seen in an expanded view, the annular groove 23 and the annular projection 25 are preferably generally linear without local directionality.

In this embodiment, the single annular groove 23 and the single annular projection 25 are provided by way of example, but the number of annular grooves 23 and the number of annular projections 25 may be one or more with no upper limits thereof. A plurality of annular grooves 23 and a plurality of annular projections 25 may be provided to be spaced a predetermined distance from each other axially of the laminate gasket 13.

The annular groove 23 preferably has a depth D of not less than 20 μm and not greater than 200 μm, more preferably not less than 35 μm and not greater than 100 μm.

In the present invention, the annular projection 25 is defined by the outer peripheral portion of the annular member 22 fixed to the inner surface 24 of the annular groove 23, whereby the annular projection 25 can be fixed to the laminate gasket 13 with a higher joining strength. Therefore, the annular projection 25 is less liable to be separated from the gasket even if the gasket is repeatedly slid in the syringe barrel. This makes it possible to ensure the higher sealability and prevent the leakage of the liquid drug.

In order to increase the joining strength, the annular groove 23 preferably has a greater depth. On the other hand, an excessively great depth of the annular groove 23 is not preferred for suppression of a damage to the laminate gasket 13. The depth of the annular groove 23 is preferably within the thickness T (about 20 μm) of the film 15 laminated on the main body 14, whereby the vulcanized rubber of the main body 14 is prevented from being exposed to the surface.

The width W2 of the annular groove 23 is preferably equal to or greater than the width W1 of the annular projection 25, but may be smaller than the width W1 of the annular projection 25.

The annular projection 25 preferably has a height H of not less than 1 m and not greater than 50 μm, more preferably not less than 15 m and not greater than 45 μm. The width W1 of the annular projection 25 is preferably not less than 1 m and not greater than 70 μm, more preferably not less than 15 μm and not greater than 45 μm.

In the present invention, only the annular projection 25 is kept in press contact with the inner peripheral surface 16 of the syringe barrel 11 around the annular projection 25, whereby a contact pressure between the laminate gasket 13 and the syringe barrel 11 can be increased. In order to increase the contact pressure, the width W1 of the annular projection 25 is preferably smaller. On the other hand, an unnecessarily fine molding process is not preferred in terms of process concerns.

Next, a production method for the laminate gasket 13 according to this embodiment will be described.

The laminate gasket 13 according to this embodiment is preferably produced through the following process steps:
(1) preparing a gasket molding mold;
(2) molding a laminate gasket having a surface laminated with a film 15 and including a film circumferential surface portion 17 in the mold;
(3) removing the laminate gasket from the mold, and then forming an annular groove 23 extending circumferentially of the film circumferential surface portion 17 of the laminate gasket;
(4) depositing a fluid material in the formed annular groove 23, and further depositing the fluid material on the annular groove 23 circumferentially of the film circumferential surface portion 17 of the laminate gasket so that the fluid material partly projects from the annular groove 23; and
(5) solidifying the fluid material to fix the fluid material in the annular groove 23 and form an annular member 22 including an annular projection 25 projecting from the surface of the film 15.

In the step of molding the laminate gasket having the surface laminated with the film 15 in the mold, an unvulcanized rubber is stacked on an inner surface of the film 15, and the resulting stack is put in the mold and vulcanization-molded.

For example, the film 15 is stacked on an unvulcanized rubber sheet containing a vulcanizing agent, and then the resulting stack is vulcanization-molded into a laminate gasket having a predetermined shape in the mold.

In this case, the inner surface of the film 15 on which the rubber is stacked is preferably preliminarily roughened. With the inner surface of the film 15 thus roughened, the rubber can firmly adhere to the film 15 by the vulcanization molding without the use of an adhesive agent or the like. The adhesion is attributable to an anchoring effect which is created with the vulcanized rubber intruding into the roughened inner surface of the film 15.

The modification of the inner surface of the film 15 may be achieved, for example, by applying an ion beam to the inner surface to break the internal molecular structure of the inner surface for the roughening (see, for example, JP4908617B).

In the step of forming the annular groove 23 extending circumferentially of the circumferential surface portion 17 of the molded laminate gasket, a known method may be used for the formation of the annular groove. A laser beam having an irradiation spot corresponding to the width W2 of the annular groove 23 is preferably used for the processing by way of example, but not by way of particular limitation. Thus, the annular groove 23 having a fine processing size can be easily formed. The laser beam is not particularly limited, but a laser beam having a smaller wavelength is preferred for a higher decomposing effect.

Where a cutting process or a laser beam process is used for the processing, in general, minute projections are liable to be formed on lateral sides of the groove. These minute projections are so-called burrs, which occur when a material is forced out of the groove to the lateral sides of the groove.

In the present invention, these minute projections are unwanted. If the heights of the minute projections are greater than the height H of the annular projection 25 of the annular member 22 to be formed later, the minute projections problematically physically interfere with the annular projection 25. Therefore, the heights of the minute projections occurring due to the processing are preferably less than the height H of the annular projection 25. For suppression of the physical interference due to the minute projections caused by the processing, only gaskets in which the heights of the minute projections are less than the height H of the annular projection 25 are selectively used.

The use of the fluid material for the annular member 22 including the annular projection 25 is advantageous in that the fluid material can be deposited in the annular groove 23 and further deposited on the annular groove along the circumference of the circumferential surface portion 17 simply by applying the fluid material. A known method such as a printing method or a spray coating method may be used as the applying method (for the deposition of the fluid material in and on the annular groove).

The fluid material is not particularly limited, as long as it is capable of withstanding the subsequent solidifying step. A fluororesin is preferred for the fluid material, because it has a smaller frictional coefficient after being solidified and, as a result, reduces the sliding resistance of the gasket in the syringe barrel. Examples of the fluid material include an emulsion containing the fluororesin and a paste prepared by dispersing the fluororesin in an organic solvent. Examples of the fluororesin include PTFE, modified PTFE, ethylene tetrafluoroethylene copolymers (ETFE), and perfluoroalkyl ether (PFA). The PTFE and the modified PTFE are particularly preferred because of their excellent slidability and chemical stability. The ETFE is preferred because of its higher resistance to Y-ray to be used for sterilization. Metal pastes are also preferred because of their excellent thermal stability and relatively low solidification temperatures.

The step of solidifying the applied fluid material is not particularly limited, but a heating method is preferably employed for the solidification. The annular member 22 is fixed to the inner surface 24 of the annular groove 23 by the heating. Thus, the annular member 22 is prevented from being separated from the gasket when the gasket is slid in the syringe barrel 11. For the heating, the laminate gasket formed with the annular member 22 is put in a heating oven.

The heating temperature is preferably not higher than 200° C., more preferably not higher than 150° C., for suppression of a damage to the laminate gasket. Another conceivable heating method which suppresses the damage to the laminate gasket is to heat only the annular member 22. A laser beam may be applied only to the annular member 22 for heating the annular member 22 by way of example, but not by way of particular limitation. The laser beam is not particularly specified, but is preferably a greater wavelength laser beam having a higher heating effect and a lower decomposing effect. In this case, the annular projection 25 may be formed as having a desired shape by applying the fluid material to a width greater than the desired width of the annular projection 25, partly heating the applied fluid material by the laser beam to solidify a desired portion of the applied fluid material, and washing off the rest of the fluid material.

Another method for the formation of the annular member 22 is to fluidize a thermoplastic resin by heating, applying the fluidized thermoplastic resin in and on the annular groove 23, and solidifying the applied thermoplastic resin by cooling.

EXAMPLES

Examples 1 to 5 and Comparative Examples 1 and 2

Laminate gaskets were each produced through vulcanization molding by using a film and an unvulcanized rubber sheet. More specifically, the film was preliminarily subjected to a surface roughening process. Then, the unvulcanized rubber sheet was stacked on the film, and the resulting stack was vulcanization-molded into the laminate gasket. Subsequently, laminate gasket products of Examples 1 to 5 were each produced by forming an annular groove in a film circumferential surface portion of the laminate gasket, depositing a fluid material in the annular groove, further depositing the fluid material on the annular groove of the film circumferential surface portion, and solidifying the fluid material. Laminate gasket products of Comparative Examples 1 and 2 were each produced by depositing the fluid material on the laminate circumferential surface portion without forming the annular groove, and solidifying the fluid material.

The laminate gasket products of Examples 1 to 5 and Comparative Examples 1 and 2 thus produced were maintained at 121° C. for 1 hour in a high-pressure steam sterilization apparatus in a cleaning step.

[Production Method]

Colorless and colored PTFE films (fluororesin CHEMFILM DF1200 available from Saint-Gobain Corporation) were used as the film.

The film surface roughening process was performed by the method described in JP4908617B. Both surfaces of the film were subjected to the surface roughening process. The thickness of the film herein used is shown in Table 1. The thickness of the film after the molding was generally reduced to about one third the original thickness.

A halogenated butyl rubber sheet was used as the unvulcanized rubber sheet.

As a vulcanizing agent, 2-di-n-butylamino-4,6-dimercapto-s-triazine (ZISNET (registered trade name) DB available from Sankyo Kasei Co., Ltd.) was used.

A vulcanization temperature of 180° C., a vulcanization period of 8 minutes, and a processing pressure of 20 MPa were employed for production conditions.

The laminate gaskets each had a product shape having a maximum diameter $\phi$ of 6.60 mm.

For the formation of the annular groove, a UV laser processing machine available from Spectronix Corporation was used. The annular groove was formed as having a desired depth and a desired width by performing a laser process a plurality of times.

Only products free from unwanted projections after being formed with the annular groove by the processing were selectively sampled through observation by means of a digital microscope (Leica DVM5000 available from Leica Microsystems Inc.) with the use of an objective lens having a magnification of 50×. The depth and the width of the annular groove are shown in Table 1.

The fluid material was deposited in the annular groove and further deposited on the annular groove for the formation of the annular projection, and then solidified after the laminate gasket was imparted with the product shape.

[Fluid Material for Annular Projection, and Deposition of Fluid Material]

Either of the following materials was used as the fluid material.

PTFE: Fluororesin dispersion (POLYFLON PTFE D210-C available from Daikin Industries, Ltd.)

Metal paste: Electrically conductive paste of thermosetting type containing silver particles (CA-6178 available from Daiken Chemical Co., Ltd.)

With the use of a micro-dispenser (available from Heishin, Ltd.), either of the fluid materials was applied onto the laminate gasket while the laminate gasket was rotated circumferentially. With the dispensing rate of the fluid material kept constant, the laminate gaskets were each rotated at different rotation speeds in Examples 1 to 5 and Comparative Examples 1 and 2.

[Heating Process]

The fluid material was deposited in and on the annular groove, and preliminarily dried at 80° C. for one hour. Then, a heating process was performed by either of the following methods:

A. Heating in oven: The heating process was performed by maintaining the laminate gasket in an oven set at a predetermined temperature (200° C. or 130° C.) for one hour.

B. Heating by laser beam: A multi-purpose manually-operable machine available from Allied Lasers, Inc. was used for the heating process. A laser beam having a wavelength of 1064 nm was emitted with the use of a hybrid laser as an oscillator. The laser beam for the heating process had a spot diameter of 10 µm.

[Test Method]

(Measurement of Dimensions of Annular Projection)

By means of a laser microscope (VK-X100 available from Keyence Corporation), the surface geometry of the laminate gasket product obtained after the solidification of the fluid material was measured with the use of an objective lens having a magnification of 50×. The maximum height and the width of the annular projection were measured at four positions on an image of the laminate gasket product, and arithmetic averages were determined for the maximum height and the width.

(Durability of Annular Projection)

The laminate gasket products thus produced were each inserted in a syringe barrel, and reciprocally moved ten times. Then, a portion of the annular projection in contact with an inner peripheral surface of the syringe barrel was observed with the use of an objective lens having a magnification of 50× by means of a digital microscope (Leica DVM5000 available from Leica Microsystems Inc.) For each of the laminate gasket products, 15 samples were prepared for the observation, and the number of samples with their annular projections separated to be brought out of contact with the inner peripheral surface of the syringe barrel was recorded. A laminate gasket product with three or less samples suffering from the separation was rated as acceptable.

TABLE 1

|  | Example 1 | Example 2 | Example 3 | Example 4 | Example 5 | Comparative Example 1 | Comparative Example 2 |
|---|---|---|---|---|---|---|---|
| Film | | | | | | | |
| Type | PTFE | PTFE | PTFE | PTFE | PTFE | PTFE | PTFE |
| Thickness (µm) | 25 | 25 | 25 | 25 | 25 | 25 | 25 |
| Annular groove | | | | | | | |
| Width (µm) | 40 | 100 | 200 | 200 | 20 | — | — |
| Depth (µm) | 40 | 100 | 200 | 200 | 50 | — | — |
| Fluid material | PTFE | PTFE | PTFE | Metal paste | Metal paste | PTFE | Metal paste |
| Annular projection | | | | | | | |
| Maximum height (µm) | 20 | 20 | 50 | 20 | 40 | 20 | 20 |
| Width (µm) | 20 | 40 | 70 | 30 | 40 | 20 | 30 |
| Heating method | A | A | B | A | B | A | A |
| Heating temperature (° C.) | 200 | 200 | — | 130 | — | 200 | 130 |
| Number of samples suffering from separation of annular projection | 0 | 1 | 3 | 1 | 0 | 5 | 4 |

[Test Results]

The laminate gasket products of Examples 1 to 5 were excellent with a significantly reduced number of samples suffering from the separation of the annular projection, as compared with the laminate gasket products of Comparative Examples 1 and 2 each produced by forming the annular projection without the formation of the annular grove after the molding of the laminate gasket.

This application claims the benefit of priority to Japanese Patent Application No. 2019-236121 filed on Dec. 26, 2019. The entire contents of this application are hereby incorporated herein by reference.

What is claimed is:

1. A method for producing a gasket for a medical syringe, the gasket producing method comprising the steps of:
    preparing a gasket molding mold;
    molding a gasket in the mold, the gasket comprising a main body having a surface laminated with a film and including a film circumferential surface portion;
    removing the gasket from the mold, and then forming an annular groove in the film circumferential surface portion of the gasket circumferentially of the film circumferential surface portion such that the annular groove has a depth greater than a thickness of the film measured from the film circumferential surface portion and extending into the main body of the gasket;
    depositing a fluid material in the formed annular groove and further depositing the fluid material on the annular groove circumferentially of the film circumferential surface portion of the gasket so that the fluid material partly projects from the annular groove; and solidifying the fluid material to fix the fluid material in the annular groove and form an annular member including an annular projection projecting from the surface of the film.

2. The gasket producing method according to claim 1, wherein the fluid material comprises a fluororesin.

3. The gasket producing method according to claim 1, wherein the fluid material comprises a metal paste.

4. The gasket producing method according to claim 1, wherein the gasket molding step comprises the step of stacking an unvulcanized rubber on an inner surface of the film in the mold, and vulcanization-molding the resulting stack.

5. The gasket producing method according to claim 4, wherein the gasket molding step comprises the step of roughening the inner surface of the film before stacking the rubber on the inner surface of the film.

6. The gasket producing method according to claim 1, wherein the annular groove forming step comprises the step of processing the circumferential surface portion of the gasket by a laser beam to remove at least a part of the film according to a shape of the annular groove.

7. The gasket producing method according to claim 1, wherein the fluid material solidifying step comprises a heating step.

8. The gasket producing method according to claim 2, wherein the fluid material solidifying step comprises a heating step.

9. The gasket producing method according to claim 3, wherein the fluid material solidifying step comprises a heating step.

10. A method for producing a gasket for a medical syringe, the gasket producing method comprising the steps of:

preparing a gasket molding mold;

molding a gasket in the mold, the gasket comprising a main body having a surface laminated with a film and including a film circumferential surface portion;

removing the gasket from the mold, and then forming an annular groove in the film circumferential surface portion of the gasket circumferentially of the film circumferential surface portion such that the annular groove has a depth greater than a thickness of the film measured from the film circumferential surface portion and extending into the main body of the gasket, the depth being in a range of 35 microns to 100 microns and the thickness being in a range of 20 microns to 50 microns;

depositing a fluid material in the formed annular groove and further depositing the fluid material on the annular groove circumferentially of the film circumferential surface portion of the gasket so that the fluid material partly projects by an amount in a range of 15 microns to 45 microns from the film circumferential surface portion; and solidifying the fluid material to fix the fluid material in the annular groove and form an annular member including an annular projection projecting from the surface of the film.

\* \* \* \* \*